(12) United States Patent
Muppa et al.

(10) Patent No.: US 8,735,613 B2
(45) Date of Patent: May 27, 2014

(54) PROCESS FOR THE MANUFACTURE OF PROPYLENE OXIDE

(75) Inventors: Prasad Muppa, Vondelingenplaat (NL); Caspar Schoolderman, Vondelingenplaat (NL); Sandra Rens Van Der Lee, Vondelingenplaat (NL); Ron Postma, Vondelingenplaat (NL)

(73) Assignee: Momentive Specialty Chemicals Inc., Columbus, OH (US)

( * ) Notice: Subject to any disclaimer, the term of this patent is extended or adjusted under 35 U.S.C. 154(b) by 0 days.

(21) Appl. No.: 13/512,167

(22) PCT Filed: Nov. 24, 2010

(86) PCT No.: PCT/EP2010/007107
§ 371 (c)(1),
(2), (4) Date: Jul. 30, 2012

(87) PCT Pub. No.: WO2011/063937
PCT Pub. Date: Jun. 3, 2011

(65) Prior Publication Data
US 2012/0289722 A1 Nov. 15, 2012

(30) Foreign Application Priority Data
Nov. 27, 2009 (EP) .................................. 09075528

(51) Int. Cl.
*C07D 301/12* (2006.01)
(52) U.S. Cl.
USPC ........................................................ 549/531
(58) Field of Classification Search
USPC ........................................................ 549/531
See application file for complete search history.

(56) References Cited

U.S. PATENT DOCUMENTS

| | | | |
|---|---|---|---|
| 4,021,454 A | 5/1977 | Wulff et al. |
| 4,038,291 A | 7/1977 | Gipson |
| 4,127,594 A | 11/1978 | Anderson et al. |
| 4,973,718 A | 11/1990 | Buchler |
| 5,153,161 A | 10/1992 | Kerschner et al. |
| 5,155,274 A | 10/1992 | Herrmann et al. |
| 5,256,779 A | 10/1993 | Kerschner et al. |
| 5,274,147 A | 12/1993 | Kerschner et al. |
| 5,329,024 A | 7/1994 | Jureller et al. |
| 5,429,769 A | 7/1995 | Nicholson et al. |
| 5,516,738 A | 5/1996 | Jureller et al. |
| 5,532,389 A | 7/1996 | Trent et al. |
| 5,833,755 A | 11/1998 | Schlon et al. |
| 6,054,407 A | 4/2000 | Schulz et al. |
| 6,087,513 A | 7/2000 | Liao et al. |
| 6,288,248 B1 | 9/2001 | Strebelle et al. |
| 6,350,888 B1 | 2/2002 | Strebelle et al. |
| 6,500,968 B2 | 12/2002 | Zhou et al. |
| 6,596,883 B2 | 7/2003 | Hofen et al. |
| 6,624,318 B1 | 9/2003 | Muller et al. |
| 6,673,950 B1 | 1/2004 | Teles et al. |
| 2001/0025695 A1 | 10/2001 | Patt et al. |
| 2002/0004606 A1 | 1/2002 | Thiele |
| 2002/0010120 A1 | 1/2002 | Hage et al. |
| 2003/0162983 A1 | 8/2003 | Strebelle et al. |
| 2006/0122409 A1 | 6/2006 | Catinat et al. |
| 2006/0167288 A1 | 7/2006 | Strebelle et al. |
| 2006/0277687 A1 | 12/2006 | Buhler et al. |
| 2010/0029848 A1 | 2/2010 | Forlin et al. |
| 2012/0316353 A1 | 12/2012 | Crampton |

FOREIGN PATENT DOCUMENTS

| | | |
|---|---|---|
| CN | 1900071 | 1/2007 |
| DE | 19923121 | 11/2000 |
| EP | 0458397 | 5/1991 |
| EP | 0458398 | 11/1991 |
| EP | 0618202 A1 | 10/1994 |
| EP | 1403219 | 3/2004 |
| EP | 1883730 | 2/2008 |
| EP | 2149569 A1 | 2/2010 |
| EP | 2149570 A1 | 2/2010 |
| EP | 2402087 | 1/2012 |
| JP | 2002145872 | 5/2002 |
| TW | 305831 | 6/1995 |
| TW | 200823183 | 6/2008 |
| WO | WO 2004/048353 A1 | 6/2004 |
| WO | WO 2005/000827 A1 | 6/2005 |
| WO | WO 2005/095370 A1 | 10/2005 |
| WO | WO 2007/046960 A1 | 4/2007 |
| WO | WO 2008/078861 A1 | 7/2008 |
| WO | WO 2008/087657 A2 | 7/2008 |
| WO | WO 2009/063487 A2 | 5/2009 |

OTHER PUBLICATIONS

De Vos D E et al., "Epoxidation of terminal or electron-deficient olefins with H2O2, catalysed by Mn-trimethyltriazacyclonane complexes in the presence of an oxalate buffer", Tetrahedron Letters, vol. 39, No. 20, (1998), pp. 3221-3224, XP-004116236.

(Continued)

*Primary Examiner* — Taylor Victor Oh

(57) ABSTRACT

A process for the manufacture of propylene oxide ("PO") by catalytic oxidation of propylene with an oxidant wherein the catalytic oxidation is performed in an aqueous reaction medium, comprising water with less than 10% by volume of cosolvents, wherein a water-soluble manganese complex is used as oxidation catalyst,
characterized in that the water-soluble manganese complex is a mononuclear species of the general formula (I):

$$[LMnX_3]Y \qquad (I)$$

or a binuclear species of the general formula (II):

$$[LMn(\mu\text{-}X)_3MnL]Y_2 \qquad (II)$$

wherein Mn is a manganese; L or each L independently is a polydentate ligand, each X independently is a coordinating species and each μ-X independently is a bridging coordinating species, whereas Y is an non-coordinating counterion, and wherein the catalytic oxidation is carried out at a pH in the range of from 1.5 to 6.0.

20 Claims, No Drawings

(56) References Cited

OTHER PUBLICATIONS

P.L. Alsters et al., "Fine-Tuning and Recycling of Homogeneous Tungstate and Polytungstate Epoxidation Catalysts", Mechanisms in Homogeneous and Heterogeneous Epoxidation Catalysis (2008) 415-428, Elsevier B.V. and Technology.
I.W.C.E. Arends et al., "Recent developments in selective catalytic epoxidations with H2O2", Topics in Catalysis, vol. 19, No. 1 (2002) 133-141.
T.H. Bennur et al., "Benzylic oxidation with H2O2 catalyzed by Mn complexes of N,H',N"-trimethyl-1,4,7-triazacyclononane: spectroscopic investigations of the active Mn Species", Journal of Molecular Catalysis A: Chemical 185 (2002) 71-80.
N.O. Brace et al., "Hydrophobic Compounds and Polymers from Long Chain Alkanamide-Formaldehyde Condensation Reactions", Journal of Organic Chemistry (1961) vol. 26, 5176-5180.
J. Brinksma et al., "Homogeneous cis-dihydroxylation and epoxidation of olefins with high H2O2 efficiency by mixed manganese/activated carbonyl catalyst system", Tetrahedron Letters 43 (2002) 2619-2622.
A.M. d'A. Rocha Gonsalves et al, "On the mechanism of carboxylic acid co-catalyst assisted metalloporphyrin oxidations" Journal of Molecular Catalysis A: Chemical 168 (2001) 25-32.
J.W. De Boer et al., "The role of salicylic acid, L-ascorbic acid, and oxalic acid in promoting the oxidation of alkenes with H2O2 catalysed by [MnIV2(O)3(tmtacn)2]2+", Royal Society of Chemistry, Dalton Transactions (2008) 6283-6295.
J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners Ipskamp BV, Enschede, the Netherlands.
D.E. De Vos et al., "Highly selective olefin epoxidation with manganese triazacyclononane complexes:impact of ligand substitution", Journal of Oganometallic Chemistry 520 (1996) 195-200.
D.E. E Vos et al., "Selective Alkene Oxidation with H2O2 and a Heterogenized Mn Catalyst: Epoxidation and a New Entry to Vicinal cis-Diols", Angew. Chem. Int. Ed. 38, No. 7 (1999) 980-983.
D.E. De Vos et al., "Epoxidation of Terminal or Electron-deficient Olefins with H2O2, catalysed by Mn-trimethyltriazacyclonane Complexes in the Presence of an Oxalate Buffer", Tetrahedron Letters 39 (1998) 3221-3224.
D.E. De Vos et al., "Highly selective epoxidation of alkenes and styrenes with H2O2 and manganese complexes of the cyclic triamine 1,4,7-trimethyl-1,4,7-triazacyclononane", Chem. Commun. (1996) 917-918.
F.C. Frostick Jr. et al., "Synthesis of Some Epoxy Vinyl Monomers by Epoxidation with Peracetic Acid", by J. Am. Chem. Soc. 81 (1958) 3350-3356.
A. Grenz et al., "Synthesis and application of novel catalytically active polymers containing 1,4,7-triazacyclononanes", Chem. Commun. (2001) No. 18, 1726-1727 (Cambridge, England).
R. Hage at al., "Bleach and oxidation catalysis by manganese-1,4,7-triazacyclononane complexes and hydrogen peroxide", Journal of Molecular Catalysis A: Chemical 251 (2006) 150-158.
N. Hoffman et al., "Liquid-Liquid Biphasic, Platinum-Catalyzed Hydrosilylation of AllyL Chloride with Trichlorosilane Using an Ionic Liquid Catalyst Phase in a Continuous Loop Reactor", Adv. Synth. Catal. (2008) 350, 2599-2609.
E. Kaczmarczyk et al., "Selective epoxidation of 1,4-bis(allyloxy)butane to 1-allyloxy-glycidoloxybutane in the presence of ionic liquids", Journal of Molecular Catalysis A: Chemical 265 (2007) 148-152.
E. Kaczmarczyk et al., "Epoxidation of 1,4-bis(allyloxy)butane by hydrogen peroxide using phase transfer catalysis", Journal of Molecular Catalysis A: Chemical 244 (2006) 173-178.
A. Murphy et al., "Ligand and pH Influence on Manganese-Mediated Peracetic Acid Epoxidation of Terminal Olefins", Organic Letters, (2004) vol. 6 No. 18, 3119-3122.
L. Ningning et al., "Epoxidation of Various Functionalized Olefins by a Ti-MWW/H2O2 Catalytic System", Chin J Catal (2008) vol. 29 Issue 2, 102-104.
G.V. Nizova et al., "Hydrocarbon Oxidations with Hydrogen Peroxide Catalyzed by a Soluble Polymer-Bound Manganese(IV) Complex with 1,4,7-Triazacyclononane", Adv. Synth. Catal. (2002) 344, No. 8, 899-905.
V.C. Quee-Smith et al., "Synthesis, Structure, and Characterization of a Novel Manganese(IV) Monomer, [MnIV(Me3TACN)(OMe)3](PF6) (Me3TACN=N,N',N"-Trimethyl-1,4,7-triazacyclononane), and Its Activity toward Olefin Oxidation with Hydrogen Peroxide", Inorganic Chemistry (1996) vol. 35, No. 22, 6461-6465.
V.B. Romakh et al., "Dinuclear Manganese Complexes Containing Chiral 1,4,7-Triazacyclononane-Derived Ligands and Their Catalytic Potential for the Oxidation of Olefins, Alkanes, and Alcohols", Inorganic Chemistry (2007) vol. 46, No. 4, 1315-1331.
J.Y. Ryu et al., "Alkane Oxidation Catalyzed by Manganese-tmtacn Complexes with H2O2", Bull. Korean Chem. Soc., (2003) vol. 24, No. 12, 1835-1837.
D.C. Sherrington et al., "Polymer-Supported Mo and V Cyclohexene Epoxidation Catalysts: Activation, Activity, and Stability", Journal of Catalysis (1991) vol. 131, 115-126.
G.B. Shul'Pin et al., "Oxidations by the system 'hydrogen Peroxide-[Mn2L2O3][PF6]2(L=1,4,7-trimethyl-1,4,7-triazacyclononane)-oxalic acid'. Part 6. Oxidation of methane and other alkanes and olefins in water", Journal of Organometallic Chemistry 690 (2005) 4498-4504.
G.B. Shul'Pin et al., "Oxidation with the 'H2O2-maganese(IV) complex-carboxylic acid' reagent", Russian Chemical Bulletin (1998) vol. 47, No. 12, 2379-2386.
K.F. Sibbons et al., "The application of manganese complexes of ligands derived from 1,4,7-triazacyclononane in oxidative catalysis" Dalton Translations (2006) 645-661, The Royal Society of Chemistry, Cambridge, England.
C. Venturello et al., "A New, Effective Catalytic System for Epoxidation of Olefins by Hydrogen Peroxide Under Phase-Transfer Conditions", Journal of Organic Chemistry (1983) vol. 48, No. 21, 3831-3833, American Chemical Society, Easton.
C.B. Woitiski et al., "Oxidations by the system 'hydrogen peroxide-dinuclear manganese(IV) complex-carboxylic acid' Part 5. Epoxidation of olefins including natural terpenes", Journal of Molecular Catalysis A: Chemical 222 (2004) 103-119.
P. Wu et al., "A novel titanosilicate with MWW structure Catalytic properties in selective epoxidation of diallyl ether with hydrogen peroxide" Journal of Catalysis 228 (2004) 183-191.
Z. Xi Et al., "An Enviromentally Benign Route for Epochlorohydrin From Allyl Chloride Epoxidation Catalyzed by Heteropolyphophatotungstate", Research on Chemical Intermediates (2007) vol. 33, No. 6, 523-534, VSP.
Aldrich, Catalog Handbook of Fine Chemicals, 1998-1999, p. 497.
R. Mbeleck et al. "Stability and recycling of polymer-supported Mo(VI) alkene epoxidation catalysts", Reactive & Functional Polymers 67 (2007) 1448-1457, Elsevier Science Publishers BV, Netherlands.
E. Kaczmarczyk et al., "Epoxidation of 1,4-diallyloxybutane to 1-allyloxy-4-glycidyloxybutane by the method of phase transfer catalysis", Journal of Molecular Catalysis A: Chemical 235 (2005) 52-56.
J.W. De Boer, "Mechanism of Cis-Dehydroxylation and Epoxidation of Alkenes by Highly H2O2 Efficient Dinuclear Managanese Catalysts." with Online Supporting Information, Inorganic Chemistry (2007), vol. 46, No. 16, pp. 6353-6372, American Chemical Society.

PROCESS FOR THE MANUFACTURE OF PROPYLENE OXIDE

FIELD OF INVENTION

The invention relates to a process for the manufacture of propylene oxide ("PO") by catalytic oxidation of propylene using hydrogen peroxide and a manganese complex.

BACKGROUND OF INVENTION

PO is an important starting material in the chemical industry. It is applied in the production of polyether polyols that are used in making polyurethane plastics. Other uses of PO include the preparation of propylene glycol, propylene glycols ethers and propylene carbonate.

The traditional route for the preparation of PO proceeds via the conversion of propylene to chloropropanols (known as "chlorohydrin process"). The reaction produces a mixture of 1-chloro-2-propanol and 2-chloro-1-propanol which are then dehydrochlorinated into PO. Lime is used as chlorine absorber in this process. This method suffers from a relatively large amount of co-produced chloride salts.

In the last 25 years PO has been prepared by epoxidation with organic hydroperoxides. The hydroperoxides are produced by homogeneous oxidation of isobutane, ethyl benzene and cumene with molecular oxygen or air. Epoxidation is accomplished by either homogeneous Mo catalysts or heterogeneous Ti-based catalysts. This technology is used by Oxirane, Halcon, ARCO (isobutane and ethylbenzene), Shell (ethylbenzene), and Sumitomo (Cumene).

Although all these processes produce PO very selectively, they suffer from the drawback of producing a co-product that needs to be isolated. This co-product then needs to be sold separately (as in the case of tert-butyl alcohol or styrene) or recycled (Cumyl alcohol), to keep the process economical. Hence these processes are multistep, and require complex facilities.

In the recent past PO processes have been developed using dilute hydrogen peroxide as an alternative to organic hydroperoxides.

For instance, from WO2005000827 a process is known for the continuous epoxidation of propene with hydrogen peroxide in the presence of a titanium silicalite catalyst and a methanol solvent, wherein the catalyst is periodically regenerated by washing with a methanol solvent at a temperature of at least 100° C. and the epoxidation reaction is carried out for periods of more than 300 h between two regeneration steps. Likewise, from U.S. Pat. No. 2002004606 a process is known for the preparation of epoxides by epoxidation of olefinic compounds with hydrogen peroxide in the presence of a titanium silicalite as a catalyst. A base is introduced into the epoxidation reactor directly or as a mixture with one or more starting substances, under pH control. A pH in the range from 4 to 9.5, preferably a pH of 5 to 9.5, is established and maintained in the reaction mixture or in the starting substance containing the base. Preferably, an aqueous-organic hydrogen peroxide solution with a pH in the range from 8 to 9 is employed and the epoxidation is carried out in a fixed bed reactor. As solvent methanol is used.

A total of about 3-7 wt % of 1-methoxy-2-propanol (or propylene glycol monomethyl ether, PGME) and propylene glycol are commonly formed in the direct epoxidation of propylene in the mixed methanol and water as solvent. Moreover, the use of organic solvents such as methanol-water or acetonitrile-water systems as solvent is disadvantage because these processes need recycle of organic solvents. Such processes require operating with complex distillation setups to separate the solvents from propylene and propylene oxide.

Furthermore, processes are known that employ Mn complexes as catalysts. Mn complexes of cyclic triamines (Mn—TmTacn complexes; "TmTacn"=1,4,7-trimethyl-1,4,7, -triazacyclononane) are known as catalysts for the epoxidation of various olefins using $H_2O_2$ as oxidant.

Of particular interest is EP0618202 (corresponding to U.S. Pat. No. 5,329,024). In EP0618202 olefins such as 4-vinylbenzoic acid, styrylacetic acid, trans-3-hexenoic acid, trans-2-hexenoic acid and allyl alcohol are epoxidised by contact with a source of oxygen and a Mn complex, preferably a dinuclear manganese complex, in which the Mn is co-ordinated to a N-containing ligand such that there is a ratio of Mn to co-ordinated N atoms of 1:3. According to this reference, the epoxidation process may be conducted in an aqueous media. When the epoxidation is conducted in an aqueous media, best results are obtained on olefins with water soluble groups. According to the examples, the epoxidation may be carried out in water, using a $NaHCO_3$ buffer with the pH adjusted to 9.0. This reference does not teach the epoxidation of propylene in water. Propylene is listed in a list separate from the olefins with water-soluble groups. Moreover, as illustrated in the attached experiments, this process utterly fails in the conversion of propylene into PO when using the recommended catalyst with the buffer in water as a solvent. A person starting from this reference, in the preparation of PO, would therefore not have considered the epoxidation of PO in water to be possible.

Another such an attempt was made in the article by Shul'pin et al. "Oxidations by the system "hydrogen peroxide—$[Mn_2L_2O_3](PF_6)_2$ (L=1,4,7-trimethyl-1,4,7-triazacyclononane)-oxalic acid". Part 6. Oxidation of methane and other alkanes and olefins in water" in Journal of Organometallic Chemistry 690 (2005) 4498. Epoxidation of 1-decene was tried to carry out in the presence of water using $[Mn_2L_2O_3]^{2+}(PF6)_2$. However the results revealed that no epoxide was produced in the absence of acetonitrile. From the examples in the articles it is clear that only after the addition of more than 50 wt % acetonitrile the epoxidation of 1-decene was initiated.

In EP2149569, by the same applicant, a process is described for the manufacture of a 1,2-epoxide by catalytic oxidation of a terminal olefin with hydrogen peroxide wherein the catalytic oxidation is performed in a biphasic system comprising an organic phase and an aqueous reaction medium, wherein a water-soluble manganese complex is used as oxidation catalyst, wherein a terminal olefin is used with a solubility at 20 DEG C of at least 0,01 to 100 g in 1 liter water, and wherein the molar ratio of terminal olefin to hydrogen peroxide is in the range of from 1:0.1 to 1:2. The epoxidation of propylene is not specifically mentioned.

Of further interest is the article by Dirk De Vos et al, "Epoxidation of Terminal or Electron-deficient Olefins with $H_2O_2$ catalysed by Mn-trimethyltriazacyclononane Complexes in the Presence of an Oxalate Buffer", in Tetrahedron Letters 39 (1998) 3221-3224. In this paper the authors produce a catalyst system that is soluble and active in acetonitrile. Next, it is shown that a catalytic amount of an oxalate/oxalic acid buffer strongly enhances the catalytic properties of Mn—TmTacn complexes. It is mentioned that especially terminal olefins are easily epoxidized. There is no suggestion to use this technology on propylene. In the light of the article by Shul'pin et al, and in particular with respect to the failed epoxidation of 1-decene, it would not be expected that epoxidation of propylene would be possible in the absence of acetonitrile. Moreover, when actually performing the epoxidation of propylene, a terminal olefin, using water as solvent (i.e., not diluted with acetonitrile) in the manner described in this article, the current inventors found that no soluble catalyst was prepared. In fact, the oxalate/oxalic acid buffer appeared to have adversely affected the catalyst. Thus, a very low yield of PO with respect to the used hydrogen peroxide was found.

In the prior art related to epoxidations with Mn—TMTACN complexes (Mono nuclear Mn—TMTACN complexes or dinuclear Mn complexes like $[Mn_2L_2O_3]^{2+}(PF6)_2$), propylene epoxidation was not studied.

A further reference of particular interest is WO2005095370. In this reference a catalytic process for the preparation of epoxides from alkenes is described, using a combination of transition metal salt, an inorganic promoter and an organic additive in absence of solvent or in the presence of a solvent with commercially available hydrogen peroxide. Styrene, indene, cyclohexene, α-pinene, and 1,2-dihydronaphthalene, were epoxidized, typically in a mixture comprising dodecane, urea and water as the reaction medium. Moreover, epoxidation of isoprene, 1-octene, tert-4-octene and chromene was conducted in the presence of acetonitrile as organic solvent in combination with water. However, when this process was repeated for the preparation of PO, using the maximum soluble amount of urea, a low PO yield with respect to the hydrogen peroxide was found.

In this respect it should be noted that the use of acetonitrile in combination with hydrogen peroxide and/or another oxidant is not without danger. In Organic Synthesis, Coll. Vol. 7, p. 126 (1990), for instance, a clear warning against the use of organic solvents and acetonitrile in particular may be found. Thus, this article starts with cautionary note that organic-soluble peroxides may be explosive.

From the above it is clear that the industry is still looking for a commercially attractive process for the manufacture of PO, in high turnover numbers and at high selectivity, meaning free of byproducts such as diols, propylene glycol monomethyl ethers and products due to the oxidation of solvents. Moreover, this process should have a high efficiency in terms of hydrogen peroxide use. This process should also allow the use of an aqueous solvent as reaction medium (meaning water with less than 10% by volume (v %), preferably less than 5 v %, more preferably less than 1 v % of co-solvents), to avoid environmental and other problems related to acetonitrile and similar organic solvents.

The present invention overcomes these disadvantages.

DISCLOSURE OF THE INVENTION

Accordingly, the invention provides a process for the manufacture of propylene oxide ("PO") by catalytic oxidation (preferably epoxidation) of propylene with an oxidant wherein the catalytic oxidation is performed in an aqueous reaction medium, comprising water with less than 10% by volume of cosolvents, wherein a water-soluble manganese complex is used as oxidation catalyst, characterized in that the water-soluble manganese complex is a mononuclear species of the general formula (I):

    (I)

or a binuclear species of the general formula (II):

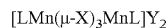    (II)

wherein Mn is a manganese; L or each L independently is a polydentate ligand, each X independently is a coordinating species and each μ-X independently is a bridging coordinating species, whereas Y is an non-coordinating counterion, and wherein the epoxidation is carried out at a pH in the range of from 1.5 to 6.0.

In a preferred embodiment, the PO or part of the PO is isolated as gas phase, which comprises PO or a mixture of propylene and PO.

MODE(S) FOR CARRYING OUT THE INVENTION

As used in the current specification, the expressions epoxidation and oxidation refer to the same reaction; the conversion of the carbon-carbon double bond of the propylene into an oxirane ring. The invention is hereafter discussed in greater detail.

It is rather surprising that the current process can be used to prepare PO at high selectivity with no noticeable amounts of byproducts (diols and such), despite having the reaction performed in an aqueous reaction medium.

In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyses. For convenience sake, and as this is common in the literature, we refer to the complex as if it is the catalyst.

Typically the catalyst comprises a manganese atom or a number of manganese atoms coordinated with a ligand or ligands. The manganese atom(s) may be in a II, III or IV oxidation state and be activated during the reaction. Of particular interest are binuclear manganese complexes. Suitable manganese complexes therefore include mononuclear species of the general formula (I):

    (I)

and binuclear species of the general formula (II):

    (II)

wherein Mn is a manganese; L or each L independently is a polydentate ligand, preferably a cyclic or acyclic compound containing 3 nitrogen atoms; each X independently is a coordinating species and each μ-X independently is a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, wherein R is a C1-C20 radical selected from the group consisting of alkyl, cycloalkyl, aryl, benzyl and combinations thereof, and Y is an non-coordinating counterion. Counterion Y may for instance be an anion selected from the group consisting of $RO^-$, $Cl^-$, $Br^-$, $I^-$, $F^-$, $SO_4^{2-}$, $RCOO^-$, $PF_6^-$, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. A preferred counterion is $CH_3COO^-$. Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The prefer ligand is TmTacn (1,4,7-trimethyl-1,4,7,-triazacyclononane), which is commercially available, for instance, from Aldrich. In this respect it is important to note that the water-solubility of the manganese catalyst is a function of all the aforementioned catalyst components.

Dinuclear manganese complexes are preferred, because of their greater activity and solubility in water. Preferred dinuclear manganese complexes are those of the formula $[Mn^{IV}_2(\mu\text{-}O)_3L_2]Y_2$, wherein L and Y have the meaning identified above, preferably TmTacn as ligand, and $CH_3COO^-$ as counterion.

According to the present invention, the manganese complex may be utilized directly or as adsorbed onto a solvent insoluble support surface. Illustrative but nonlimiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex is used in catalytically effective amounts. Typically, the catalyst is used in a molar ratio of catalyst (Mn) versus hydrogen peroxide of from 1:10 to 1:10,000,000, preferably of from 1:20 to 1:100,000, most preferably of from 1:50 to 1:50000. An advantage of the current invention, using a water soluble manganese complex is that the catalyst essentially does not migrate to the organic phase.

The aqueous reaction medium typically is a water phase containing propylene and/or propylene oxide and less than 10% by volume, preferably only minor amounts, if any, of other organic compounds. Although not preferred, the reaction medium may contain minor amounts of co-solvents such as methanol and acetone and the like. Whilst excluding the presence of propylene and/or PO, the aqueous reaction medium therefore suitably comprises at least 90% by volume of water, preferably 95 v %, more preferably 99 v %, still more preferably 99,9 v % of water. Most preferably, however, the aqueous reaction medium (again, excluding any propylene and/or propylene oxide dissolved therein) is essentially a 100% water phase.

The aqueous reaction medium will contain a buffer system so as to stabilize the pH. For instance, it has been found that the aqueous reaction medium is suitably stabilized in a pH range of 1.5 to 6.0, whereas the preferred pH range is between 1.5 and 5.0 and the most preferred is between 2.0 and 4.0.

The suitable or preferred range may be achieved by several known organic acid-salt combinations, with the preferred combination being based on oxalic acid-oxalate salt, or acetate acid-acetate salt (3.7 to 5.6) or oxalic acid-oxalate salt and acetic acid-acetate salt. When oxalic acid and sodium oxalate are used, the pH ratio may be varied from 2.0 to 6.0. Typically, this buffer may be used in a molar ratio to the catalyst of about 10:1, but the amounts may be varied broadly, e.g., ranging from 1:1 to 100:1. The buffer may also modify the manganese complexes to form buffer modified bridging coordinating species $(\mu\text{-}X)'$. Examples of such bridging coordinating species made from buffer materials include $[OOC-COOH]^{1-}$, $[OOC-COO]2-$, $[OOCC-R-CCOOH]1-$, $[OOCC-R-CCOO]2-$, and combinations thereof. The modified bridging coordinating species may comprise one or more of the available bridging coordinating specie positions in the structures of the manganese complexes described herein. For example, the bridging coordinating species of $[OOC-COOH]^{1-}$, may form two of the three bridging coordinating species of the manganese complex described herein in a solution having an oxalate oxalic acid-oxalate salt buffer.

The aqueous reaction medium may also contain a phase transfer agent and/or a surfactant. Known phase transfer agents that may be used in the process of the invention include quaternary alkyl ammonium salts. Known surfactants that may be used in the process of the invention include non ionic surfactants such as Triton X100™ available from Union Carbide.

It is believed to be beneficial that the aqueous reaction medium contains at least trace amounts of propylene. Although this is purely a hypothesis, it is believed that the presence of propylene allows the catalyst to remain active, whereas it is believed that without the presence of propylene and/or due to the presence of PO and/or oxidant without propylene present the activity of the active catalyst reduces.

The reaction conditions for the catalytic oxidation may be quickly determined by a person skilled in the art. The epoxidation is carried out either under pressure or at atmospheric pressure. The reaction is believed to be exothermic, and cooling of the reaction medium may be required. The reaction is preferably carried out at temperatures anywhere from 5° C. to 40° C., preferably from 5° C. to 30° C.

To achieve the high selectivity and turnover numbers of the current invention, catalyst and oxidant are preferably combined (for reaction with the propylene) at a molar ratio of from 1:100 to 1:10,00,000, more preferably of from 1:500 to 1:100,000, still more preferably of from 1:1000 to 1:50,000.

The molar ratio of propylene to hydrogen peroxide is very important in the process of the current invention. If too much hydrogen peroxide is used, then the selectivity towards the desired epoxide reduces due to the production of undesirable side-products, such as propan-1,2-diol, or involves a significant waste of the oxidant. If not enough hydrogen peroxide is used, then the turnover number is suboptimal. This is therefore significantly different from bleaching conditions described in the prior art, where excessive amounts of hydrogen peroxide are used. Propylene may be preferably used in excess over the oxidant. The molar ratio of propylene to hydrogen peroxide may be in the range of from greater than 1:2 to about 10:1, such as from about 1:1 to about 10:1 (or alternatively, from about 1:1.2 to about 2:1), for example, about 1:1. The yield of epoxide with respect to peroxide utilization is from about 70% to about 99.7%, for example, about 89%. The conversion of propylene into PO is discussed hereinafter. Depending on the reaction conditions, the reaction may be performed in one phase, i.e., aqueous phase or a two layer system comprising an organic phase and an aqueous phase.

The state of reaction mixture in the presence of propylene under reaction conditions is discussed hereafter.

If propylene is fed at a rate whereby the concentration is below its maximum solubility in the reaction medium and PO is formed in an amount whereby the concentration is below its maximum solubility in the reaction medium then the reaction system is in a single phase.

If however propylene is fed at a rate that the concentration is above its maximum solubility in the reaction medium then depending on the reaction temperature and pressure, propylene will form a separate gas or liquid phase. For example, propylene has a solubility (expressed in grams per liter water at 20° C.) of about 0.4 g/L at a partial pressure of 1 bar. The solubility of the propylene may change under different partial pressure conditions when propylene is introduced as a gas phase or under the conditions described hereafter.

At low pressure and/or high temperature conditions (e.g. above 10° C. and 1 Bar) propylene can form a separate gas phase. The propylene that leaves the reaction medium is preferably recycled. In the case of sufficiently low pressure and/or high temperature conditions PO formed during the reaction may come out of the reaction medium as a gas as well (e.g. above 40° C. and 1 Bar). This is advantageous in that the PO is stripped from the reaction mixture together with the recycled propylene gas. The PO is recovered from the process by cooling the recycled propylene. In that case PO will be removed from the process by condensation. However other methods of PO removal, as known by people skilled in the art, are not excluded from this invention. Such methods may be needed if the pressure and temperature conditions are sufficient to cause propylene to be present as a gas but insufficient to cause PO to come out. The propylene oxide then remains dissolved in the reaction medium or even forms a separate organic phase if the concentration exceeds solubility.

If the pressure is high enough (e.g. 30 Bar) to liquefy the propylene, and if the propylene exceeds its maximum solubility in the reaction medium then propylene will be present as a separate organic phase. In this case the PO formed during the reaction may be dissolved in the reaction medium, and/or dissolved in the propylene phase (organic phase). Reaction conditions where parts or the whole reaction mixture becomes super critical are also part of this invention.

Preferably, propylene is finely dispersed as a gas into the reaction medium, propylene being fed in excess and the excess propylene leaving the reaction medium as a gas to be recycled. Most preferably the reaction temperature and pressure, as well as the PO concentration are selected such that the PO formed during the reaction leaves the reaction medium as a gas. More preferably the PO leaves the reaction medium being stripped by the propylene recycle and the PO being recovered from the propylene recycle by means of condensation.

Most preferably, the reaction is carried out at temperatures in the range from 5° C. and 40° C. and at pressures in the range from 0.9 to 9 bar.

The catalytic oxidation of the present invention is carried out preferably using hydrogen peroxide as oxidant. Other oxidants may be used, i.e. as precursor to the hydrogen peroxide, but given the availability and to reduce environmental impact hydrogen peroxide is the preferred oxidant. Hydrogen peroxide has strong oxidizing properties. As bleaching agent it is mostly used for bleaching paper. It is typically used in an aqueous solution. The concentration of hydrogen peroxide may vary, from 15% (e.g., consumer grade for bleaching hair) to 98% (propellant grade), with a preference for industrial grades varying from 20 to 60%, preferably from 30 to 50%.

To ensure optimal oxidant efficiency, the oxidant is preferably added to the aqueous reaction medium at a rate about equal to the reaction rate of the catalytic oxidation.

The catalytic oxidation may be performed in a batch process, in a continuous process or in a semi-continuous process. Indeed, the process may be modified in various aspects without departing from the gist of the invention.

By way of general example the catalytic oxidation of propylene is described hereafter.

The catalytic oxidation may be performed in a common stirred tank reactor provided with a means of stirring. For instance, this may be a common explosion-proof blade agitator operating under an agitation speed of around 400 rpm. The catalyst, aqueous reaction medium and reactants may be added in batch, or the reactants may be added over a period of time. If hydrogen peroxide is added during the reaction, then it is added to either the (stirred) organic phase comprising the propylene or the (stirred) aqueous reaction medium.

In (semi)continuous operations, various recycling streams may be used to control the reaction conditions (maintained at a temperature of between 5° C. and 40° C.) and to optimize the production rate.

The following examples will more fully illustrate selected embodiments of this invention. All parts, percentages and proportions referred to herein and in the appended claims are by weight unless otherwise indicated.

EXPERIMENTAL

The catalytic oxidation was carried out with a binuclear manganese complex as catalyst of the formula:

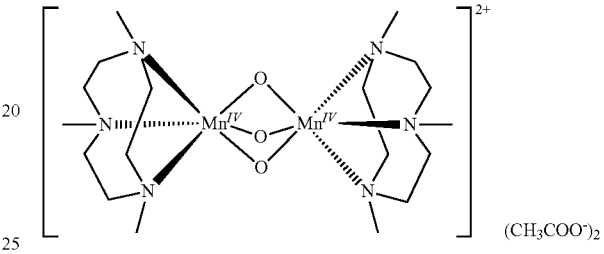

In the examples according to the invention an oxalate/oxalic acid buffer was used, with 35% aqueous $H_2O_2$ as oxidant, and water (pure) as aqueous reaction medium. The experiments were carried out with propylene as the terminal olefin.

Example 1

Catalytic epoxidation of propylene was carried out with $[(TmTacn)_2 Mn^{IV}{}_2(\mu\text{-}O)_3]^{2+}(CH_3COO^-)_2$ as catalyst at 5° C. in a four necked glass reactor facilitated with a mechanical stirrer, cooling jacket and a bottom valve. A sparger (porous) was used to send propylene into the reactor in the form of fine micro bubbles. The gas outlet of the reactor was connected to a cold trap to collect the product, propylene oxide. Water was used as solvent in the cold trap to collect the propylene oxide. An outlet was arranged to the cold trap for the safe passage of unreacted propylene, for re-use in the epoxidation.

The molar ratio of propylene: hydrogen peroxide: catalyst: co-catalysts was excess propylene (excess propylene to hydrogen peroxide, thus, greater than 4300): 4300: 1:59.

About 69 μmol of catalyst was added in 140 mL of water followed by the addition of 2 mmol of sodium oxalate in 80 mL of $H_2O$ and 2 mmol of oxalic acid in 80 mL of $H_2O$ into the glass reactor under stirring conditions. The catalyst and buffer were stirred for 10 minutes before the start of the dosage of the propylene. The reaction was initiated with the addition of dilute $H_2O_2$ as oxidant. Total 300 mmol of oxidant was added with a flow rate of 10 mL/h into the reaction solution. Dosing of oxidant was completed in first 2.8 h and the reaction was continued for the complete 3 h time period. After the reaction the aqueous solution in the reactor was analyzed to determine the residual level of $H_2O_2$. The unreacted hydrogen peroxide in the reactor was killed with $Na_2SO_3$. Then the aqueous solution in the reactor and the aqueous solution in the cold trap were analyzed by GC.

The total amount of PO obtained from the two solutions was 15.5 g, which corresponds to 266 mmol for the theoretical maximum production of 300 mmol. The only by-product formed in the reaction was propan-1,2-diol, however at a negligible amount of 0.06 g (corresponding to 0.76 mmol). At the end of the reaction 0.06 wt % of the $H_2O_2$ was left over in the reaction mixture corresponds to 6 mmol. The selectivity of propylene oxide is 99.7% and the yield of epoxide with respect to peroxide utilization is 89%.

Example 2 (Comparative Experiment)

Catalytic epoxidation of propylene was carried out similar to example 1 above, however with $[(TMTACN)_2 Mn^{IV}_2 (\mu-O)_3]^{2+}(PF_6)_2$ in the presence of $NaHCO_3$ buffer as mentioned in Example 1 of EP0618202 A1. Propylene gas was continuously send as fine micro bubbles into the reactor containing 300 mL of 0.1 M $NaHCO_3$ buffer and 0.008 M of $[(TMTACN)_2 Mn^{IV}_2(\mu-O)_3]^{2+}(PF_6)_2$ catalyst. Reaction is initiated with the addition of 35 wt % hydrogen peroxide in water. Total 300 mmol of dilute $H_2O_2$ was added at 10 mL/h flow rate for 2.8 h and the reaction is continued for 3 h. Like in example 1 after the reaction, the aqueous solution in the reactor and the aqueous solution in the cold trap were analyzed by GC. The left over hydrogen peroxide in the reactor is found to be 92 mmol. The PO produced during the reaction was lower than 1%. Total 208 mmol of $H_2O_2$ was decomposed into the $H_2O$ and $O_2$ during the reaction of 3 h.

Example 3 (Comparative Experiment)

Catalytic epoxidation of propylene was carried out similar to example 1 above, however with the in-situ catalyst system obtained by $MnSO_4$, TmTacn in oxalate buffer as mentioned in Table 1 of the De Vos article in Tetrahedron Letters 39 (1998) 3221. It should be noted that a soluble catalyst system could be produced in-situ only when using acetonitrile as solvent. On the other hand, when the method was repeated using water as solvent, no soluble catalyst was formed.

To 300 mL of water, 0.45 mmol of TmTacn ligand, 0.3 mmol of $MnSO_4$ followed by 0.45 mmol of oxalic acid and 0.45 mmol of sodium oxalate buffer were added under stirring conditions. The molar ratio of propylene: $MnSO_4$:TMTACN: co-catalyst: $H_2O_2$ was excess: 1:1.5:1000. Total 300 mmol of 35 wt % dilute $H_2O_2$ was added at a flow rate of 10 mL/h for 2.8 h and the reaction is continued for 3 h. The PO produced during the reaction was 2.8 g of PO, which corresponds to 48 mmol and 0.04 mmol of propane-1,2- diol. By the end of the reaction the left over $H_2O_2$ was determined at 275 mmol. The selectivity of propylene oxide is 99.9%. However the yield of epoxide with respect to the added hydrogen peroxide is only 16%.

Example 4 (Comparative Experiment)

Catalytic epoxidation of propylene was carried out similar to example 1 above, however with the catalyst system used in example 1 of WO 2005/095370, both with and without urea.

To 300 mL of water, 0.0006 mol of $MnSO_4.H_2O$, 0.18 mol of $NaHCO_3$ followed by 0.08 mol of dodecane were added under stirring conditions. Total 300 mmol of 35 wt % $H_2O_2$ in water was added at a flow rate of 10 mL/h for 2.8 h. The reaction is continued for 3 h. The PO produced during the reaction was 2.1 g of PO corresponds to 37 mmol. Selectivity of PO is 97%. The yield of epoxide with respect to peroxide added is only 13%. At the end of the reaction the left over hydrogen peroxide in the reaction mixture is 3 mmol.

When 5 mol of urea was added (the maximum amount of urea that was soluble in water), the PO produced during the reaction was 6 g, which corresponds to 103 mmol. Selectivity of PO is 100%. The yield of epoxide relative to the added hydrogen peroxide increased as a result of the added urea, but remained low at 34%. At the end of the reaction the left over hydrogen peroxide in the reaction mixture is 2 mmol.

Results and Discussion

Example 1

Example 1 is an example in accordance with the present invention. In example 1, the yield of epoxide with respect to the added hydrogen peroxide was 89% at 99.7% selectivity of PO. Major amount of the formed PO was present in the reaction mixture under the present experimental conditions and only small amount of PO was evaporated and collected in the cold trap.

Although the solubility of propylene is low in water (0.7 g/L at 5° C. and atmospheric pressure, the conditions for example 1), the epoxidation of propylene surprisingly occurred due to the high activity of the current catalyst system without hindrance.

Example 2

The catalyst system of EP0618202 is active in water for water-soluble olefins. A scouting experiment with propylene would teach a person skilled in the art that it is not suitable for water insoluble olefins like propylene. Rather, the catalyst system is active in the catalytic decomposition of $H_2O_2$.

A person skilled in the art would therefore have had no reasons to assume the catalytic epoxidation of propylene in water could be carried out.

Example 3

A person skilled in the art would have found the catalyst of the De Vos article to be of academic interest only. The method therein disclosed results in a soluble catalyst when using acetonitrile as solvent, but not when water was used as solvent. Indeed, the buffer system appears to act adversely when trying to prepare a soluble catalyst. Since it did not form a soluble catalyst, Example 3 is outside the current scope of the invention. Anyway, the yield of epoxide with respect to the added hydrogen peroxide was only 16%. Moreover, there is evidence that the epoxidation occurred only at the end of the reaction process, while the left over amount of hydrogen peroxide was killed, which thus is a very inefficient manner of using the hydrogen peroxide as reactant.

Example 4

The catalyst system in comparative example 4 efficiently decomposed the large amount (260 mmol) of $H_2O_2$ into $H_2O$ and $O_2$. Moreover, the reaction mixture in this system is not 100% water as it contains dodecane (5 wt % in water).

Urea appears to help to improve the epoxidation, possibly by the formation of urea hydrogen peroxide, which then acts as an oxidant for the epoxidation. Use of (large amounts of) urea, however, is simply not economic.

The invention claimed is:

1. A process for the manufacture of propylene oxide, comprising reacting propylene with an oxidant in the presence of a catalyst, in an aqueous reaction medium, comprising water with less than 10% by volume of cosolvents, wherein the catalyst comprises a water-soluble manganese complex which is a mononuclear species of the formula (I):

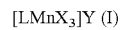

or a binuclear species of the formula (II):

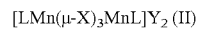

wherein Mn is a manganese; L or each L independently is a polydentate ligand, each X independently is a coordinating species and each μ-X independently is a bridging coordinating species, and Y is an non-coordinating counterion, and wherein the oxidation is carried out at a pH in the range of from 1.5 to 6.0, and wherein the molar ratio of propylene to the oxidant is from 10:1 to 1:1.

2. The process of claim 1 wherein the catalyst comprises a mononuclear manganese complex of the formula (I):

[LMnX$_3$]Y (I)

or a binuclear manganese complex of the formula (II):

[LMn(μ-X)$_3$MnL]Y$_2$ (II)

wherein Mn is a manganese; L or each L independently is a polydentate ligand; each X independently is a coordinating species and each μ-X independently is a bridging coordinating species, selected from the group consisting of: RO$^-$, Cl$^-$, Br$^-$, I$^-$, F$^-$, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$—C$_{20}$ radical selected from the group consisting of alkyl, cycloalkyl, aryl, benzyl and combinations thereof, and Y is an non-coordinating counterion.

3. The process of claim 2, wherein each polydentate ligand is independently selected from acyclic compounds having at least 7 atoms in the backbone or cyclic compounds having at least 9 atoms in the ring, each having the nitrogen atoms separated by at least two carbon atoms.

4. The process of claim 1, wherein a binuclear water-soluble manganese complex is used as the catalyst.

5. The process of claim 1, wherein the catalyst is used in a molar ratio of the catalyst (Mn) to the oxidant from 1:100 to 1:10,000,000.

6. The process of claim 1, wherein the aqueous reaction medium is a water phase.

7. The process of anyone claim 1, wherein the aqueous reaction medium further comprises a buffer system.

8. The process of claim 1, wherein the reaction is carried out at a temperature of from about 5° C. to about 40° C. and at pressures from about 0.9 to about 9 bar.

9. The process of claim 1, wherein the oxidant comprises hydrogen peroxide.

10. The process of claim 1, wherein the reaction medium is an aqueous phase and the propylene is a dispersed gas phase dissolved in a liquid phase.

11. The process of claim 1, wherein the reaction medium is a liquid phase and the propylene is present as a dispersed gas phase and a portion of the prolylene oxide leaves the reaction medium as a gas along with unreacted propylene.

12. The process of claim 1, wherein the reaction medium is an aqueous phase and the propylene can also be present as a separate liquid phase.

13. The process of claim 1, wherein the reaction medium is an aqueous phase and the propylene and the propylene oxide are present as a separate liquid phase.

14. The process of claim 1, wherein the oxidant is added to the aqueous reaction medium at a rate about equal to the reaction rate of the oxidation.

15. The process of claim 1, wherein the oxidation is performed in a batch process, in a continuous process or in a semi-continuous process.

16. The process of claim 1, wherein the oxidant comprises hydrogen peroxide, and the ratio of propylene to the hydrogen peroxide is from about 10:1 to about 1:1.

17. The process of claim 1, wherein the aqueous reaction medium comprises a 100% aqueous medium excluding any dissolved epoxide and terminal olefin.

18. The process of claim 1, wherein the aqueous reaction medium further comprises a pH in the range of from 2 to 5.

19. The process of claim 1, wherein the buffer system comprises an acid-salt combination.

20. The process of claim 19, wherein the acid-salt combination comprises oxalic acid-oxalate salt.

* * * * *